(12) United States Patent
Barth et al.

(10) Patent No.: US 7,618,995 B2
(45) Date of Patent: Nov. 17, 2009

(54) DERIVATIVES OF 4,5-DIARYLPYRROLE, PREPARATION METHOD THEREOF AND USE OF SAME IN THERAPEUTICS

(75) Inventors: Francis Barth, Saint Georges D'Orques (FR); Christian Congy, Saint Gely du Fesc (FR); Laurent Hortala, Montpellier (FR); Murielle Rinaldi-Carmona, Saint Georges D'Orques (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/952,224

(22) Filed: Dec. 7, 2007

(65) Prior Publication Data

US 2008/0176924 A1 Jul. 24, 2008

Related U.S. Application Data

(63) Continuation of application No. PCT/FR2006/001416, filed on Jun. 22, 2006.

(30) Foreign Application Priority Data

Jun. 27, 2005 (FR) .................... 05 06609

(51) Int. Cl.
*A61K 31/40* (2006.01)
*C07D 207/30* (2006.01)
(52) U.S. Cl. ...................... 514/427; 548/563
(58) Field of Classification Search ............ 514/427; 548/563
See application file for complete search history.

(56) References Cited

U.S. PATENT DOCUMENTS

| 4,335,136 A | 6/1982 | Cherkofsky et al. |
| 5,935,990 A | 8/1999 | Khanna et al. |
| 7,381,727 B2 * | 6/2008 | Barth et al. ............ 514/254.01 |

FOREIGN PATENT DOCUMENTS

WO    WO 2004/058249    7/2004

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
Lange, J. H. M., et. al., Medicinal Chemistry Strategies to CB1 Cannabinoid Receptor Antagonists, Drug Discovery Today, vol. 10, No. 10, pp. 693-702.

* cited by examiner

*Primary Examiner*—Kamal A Saeed
*Assistant Examiner*—Samantha L Shterengarts
(74) *Attorney, Agent, or Firm*—Balaram Gupta

(57) ABSTRACT

The invention relates to compounds having formula (I):

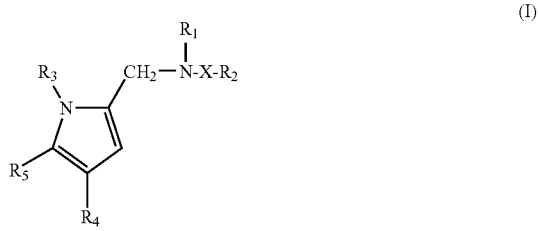

Wherein X, $R_1$, $R_2$, $R_3$, $R_4$ and $R_5$ are as defined herein. The invention also relates to the preparation method thereof and the use of same in therapeutics.

12 Claims, No Drawings

DERIVATIVES OF 4,5-DIARYLPYRROLE, PREPARATION METHOD THEREOF AND USE OF SAME IN THERAPEUTICS

This application is a continuation of International application No. PCT/FR2006/001,416, filed Jun. 22, 2006, which is incorporated herein by reference in its entirety; which claims the benefit of priority of French Patent Application No. 05/06,609, filed Jun. 27, 2005.

The present invention relates to 4,5-diarylpyrrole derivatives, to the method for preparing them and to their therapeutic use.

U.S. Pat. No. 4,335,136 and European patent EP 0 038 536 describe 4,5-diaryl-alpha-(polyfluoroalkyl)-1H-pyrrole-2-methanamine derivatives exhibiting anti-inflammatory properties.

Patent application WO 2005/058249 describes diarylpyrrole derivatives as cannabinoid receptor modulators and patent application WO 2003/027 069 describes diarylpyrrole derivatives that act on obesity.

Novel 4,5-diaryl-2-aminomethylpyrrole derivatives which have cannabinoid $CB_1$ receptor antagonist properties have now been found, located centrally and/or peripherally.

A subject of the present invention is compounds corresponding to formula (I):

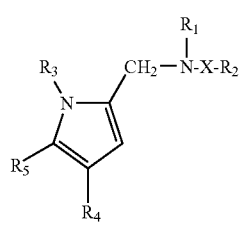

in which:
X represents a group

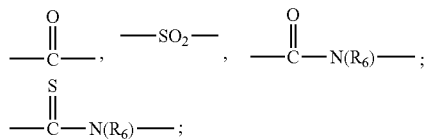

$R_1$ represents a hydrogen atom or a $(C_1-C_4)$alkyl group;
$R_2$ represents:
- a $(C_1-C_{12})$alkyl which is unsubstituted or substituted one or more times with substituents chosen independently from a halogen atom, a hydroxyl, a $(C_1-C_4)$ alkoxy, a $(C_1-C_4)$alkylthio, a phenoxy, a trifluoromethoxy radical, a difluoromethoxy radical, a difluoromethylthio radical and a trifluoromethylthio radical;
- a nonaromatic carbocyclic $(C_3-C_{12})$ radical which is unsubstituted or substituted one or more times with substituents chosen independently from a $(C_1-C_4)$ alkyl, a $(C_1-C_4)$alkoxy, a $(C_1-C_4)$alkylthio, a fluorine atom, a hydroxyl, a trifluoromethyl radical, a difluoromethyl radical, a trifluoromethoxy radical, a difluoromethoxy radical, a trifluoromethylthio radical and a difluoromethylthio radical;
- a methyl substituted with a nonaromatic carbocyclic $(C_3-C_{12})$ radical which is unsubstituted or substituted one or more times with substituents chosen independently from a $(C_1-C_4)$ alkyl, a $(C_1-C_4)$ alkoxy, a $(C_1-C_4)$alkylthio, a fluorine atom, a hydroxyl, a trifluoromethyl radical, a difluoromethyl radical, a trifluoromethoxy radical, a difluoromethoxy radical, a trifluoromethylthio radical and a difluoromethylthio radical;
- a phenyl, benzyl, benzhydryl or benzhydrylmethyl radical, in which each phenyl group is unsubstituted or substituted one or more times with substituents chosen independently from a halogen atom, a hydroxyl, a $(C_1-C_4)$ alkyl, a $(C_1-C_4)$ alkoxy, a methylenedioxy, a cyano, a nitro, a trifluoromethyl, a difluoromethyl, a difluoromethoxy, a trifluoromethoxy, a trifluoromethylthio, a difluoromethylthio, an $S(O)_n$Alk group, an $OS(O)_n$Alk group and a $(C_1-C_4)$ alkylcarbonyl group;
- a phenyl radical substituted with a heterocyclic radical chosen from pyrrolyl, imidazolyl, pyridyl or pyrazolyl, said heterocyclic radical being unsubstituted or substituted one or more times with one or more substituents chosen independently from a halogen atom or a $(C_1-C_4)$alkyl group;
- a phenyl radical substituted with a phenyl or a phenoxy, in which each phenyl group is unsubstituted or substituted one or more times with substituents chosen independently from a halogen atom, a hydroxyl, a $(C_1-C_4)$alkyl, a $(C_1-C_4)$alkoxy, a methylenedioxy, a cyano, a nitro, a trifluoromethyl, a difluoromethyl, a difluoromethoxy, a trifluoromethoxy, a trifluoromethylthio, a difluoromethylthio, an $S(O)_n$Alk group, an $OS(O)_n$Alk group and a $(C_1-C_4)$ alkylcarbonyl group;
- a 1,2,3,4-tetrahydronaphthalen-2-yl which is unsubstituted or substituted one or more times with a $(C_1-C_4)$ alkyl or a trifluoromethyl;
- a pyrrolyl, imidazolyl, pyridyl, pyrazolyl, furyl, thienyl, oxazolyl or thiazolyl radical, said radicals being unsubstituted or substituted with one or more substituents chosen independently from a halogen atom, a $(C_1-C_4)$alkyl group or a trifluoromethyl group;
- an indol-2-yl or an N-methylindol-2-yl;

$R_3$ represents a $(C_1-C_5)$alkyl or a $(C_3-C_7)$cycloalkyl;
$R_4$ represents a phenyl which is unsubstituted or substituted one or more times with substituents chosen independently from a halogen atom, a $(C_1-C_4)$alkyl, a $(C_1-C_4)$alkoxy, a cyano, a difluoromethyl radical, a trifluoromethyl radical, a difluoromethoxy radical, a trifluoromethoxy radical, an $S(O)_n$Alk group or an $OS(O)_n$Alk group;
$R_5$ represents a phenyl which is unsubstituted or substituted one or more times with substituents chosen independently from a halogen atom, a $(C_1-C_4)$alkyl, a $(C_1-C_4)$alkoxy, a cyano, a difluoromethyl radical, a trifluoromethyl radical, a difluoromethoxy radical, a trifluoromethoxy radical, an $S(O)_n$Alk group or an $OS(O)_n$Alk group;
$R_6$ represents a hydrogen atom or a $(C_1-C_4)$alkyl;
n represents 0, 1 or 2;
Alk represents a $(C_1-C_4)$alkyl.

The compounds of formula (I) may comprise one or more asymmetric carbon atoms. They may therefore exist in the form of enantiomers or of diastereoisomers. These enantiomers and diastereoisomers, and also mixtures thereof, including racemic mixtures, are part of the invention.

The compounds of formula (I) may exist in the form of hydrates or of solvates, i.e. in the form of associations or of combinations with one or more molecules of water or with a solvent. Such hydrates and solvates are also part of the invention.

The term "halogen atom" is intended to mean a bromine, chlorine, fluorine or iodine atom.

The term "$(C_1-C_4)$alkyl" or respectively "$(C_1-C_5)$alkyl" or "$(C_1-C_7)$alkyl" is intended to mean a linear or branched alkyl radical containing from one to four carbon atoms or respectively from one to five carbon atoms or from one to seven carbon atoms, such as a methyl, ethyl, propyl, isopropyl, butyl, isobutyl, sec-butyl, tert-butyl, pentyl, isopentyl, hexyl, isohexyl or heptyl radical.

The term "$(C_1-C_4)$alkoxy" is intended to mean a linear or branched alkoxy radical having from one to four carbon atoms, such as a methoxy, ethoxy, propoxy, isopropoxy, butoxy, sec-butoxy or tert-butoxy radical.

The term "nonaromatic carbocyclic $C_3-C_{12}$ radical" is intended to mean a monocyclic radical or a condensed or bridged di- or tricyclic radical; the term "monocyclic radical" is intended to mean a cycloalkyl, for example cyclopropyl, cyclobutyl, cyclopentyl, cyclohexyl or cycloheptyl, cyclopentyl, cyclohexyl and cycloheptyl radicals being preferred; the term "condensed or bridged di- or tricyclic radical" is intended to mean, for example, bicyclo[2.2.1]heptyl, bicyclo[2.2.2]octyl, bicyclo[3.2.1]octyl or adamantyl.

Most particularly, a subject of the present invention is compounds of formula (I) in which:

X represents a group

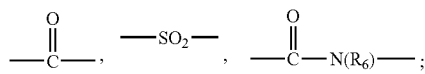

$R_1$ represents a hydrogen atom or a $(C_1-C_4)$alkyl group;

$R_2$ represents:
- a $(C_1-C_7)$alkyl;
- a nonaromatic carbocyclic $C_3-C_{12}$ radical which is unsubstituted or substituted one or more times with a $(C_1-C_4)$alkyl group;
- a methyl substituted with a nonaromatic carbocyclic $C_3-C_{12}$ radical which is unsubstituted or substituted one or more times on the carbocycle with a $(C_1-C_4)$alkyl;
- a phenyl which is unsubstituted or substituted one or more times with substituents chosen independently from a halogen atom, a $(C_1-C_4)$alkyl, a hydroxyl, a $(C_1-C_4)$alkoxy, a cyano, a trifluoromethyl group, a trifluoromethoxy group, an $S(O)_n$Alk group and a $(C_1-C_4)$alkylcarbonyl group; or from a phenyl, phenoxy, pyrrolyl, imidazolyl, pyridyl or pyrazolyl radical, said radicals being unsubstituted or substituted one or more times with a $(C_1-C_4)$alkyl;
- a benzyl which is unsubstituted or substituted one or more times on the phenyl with substituents chosen independently from a halogen atom, a cyano, a $(C_1-C_4)$alkyl, a $(C_1-C_4)$alkoxy, a trifluoromethyl radical or an $S(O)_n$Alk group; or substituted in the alpha-position with one or two similar or different groups chosen from a $(C_1-C_4)$alkyl and a $(C_3-C_7)$cycloalkyl;
- a benzhydryl or a benzhydrylmethyl group;
- a 1,2,3,4-tetrahydronaphthalen-2-yl which is unsubstituted or substituted one or more times with a $(C_1-C_4)$alkyl;
- a pyrrolyl, imidazolyl, pyridyl, pyrazolyl, furyl or thienyl radical, said radicals being unsubstituted or substituted with one or more substituents chosen independently from a halogen atom or a $(C_1-C_4)$alkyl group;
- an indol-2-yl or an N-methylindol-2-yl;

$R_3$ represents a $(C_1-C_5)$alkyl or a $(C_3-C_7)$cycloalkyl;

$R_4$ represents a phenyl which is unsubstituted or substituted one or more times with substituents chosen independently from a halogen atom, a $(C_1-C_4)$alkyl, a $(C_1-C_4)$alkoxy, a trifluoromethyl radical or an $S(O)_n$Alk group;

$R_5$ represents a phenyl which is unsubstituted or substituted one or more times with substituents chosen independently from a halogen atom, a $(C_1-C_4)$alkyl, a $(C_1-C_4)$alkoxy, a trifluoromethyl radical or an $S(O)_n$Alk group;

$R_6$ represents a hydrogen atom or a $(C_1-C_4)$alkyl;

n represents 0, 1 or 2;

Alk represents a $(C_1-C_4)$alkyl.

Among the compounds of formula (I), which are subjects of the invention, the following are distinguished:
- the compounds of formula (IA) in which —X— represents a —CO— group and the substituents $R_1$ to $R_5$ are as defined for the compounds of the formula (I);
- the compounds of formula (IB) in which —X— represents an —$SO_2$— group and the substituents $R_1$ to $R_5$ are as defined for the compounds of formula (I);
- the compounds of formula (IC) in which —X— represents a —$CON(R_6)$— group and the substituents $R_1$ to $R_6$ are as defined for the compounds of formula (I);
- the compounds of formula (ID) in which —X— represents a —$CSN(R_6)$— group and the substituents $R_1$ to $R_6$ are as defined for the compounds of formula (I).

Among the compounds which are the subjects of the invention, preference is given to the compounds of formula (I) in which:

$R_1$ represents a hydrogen atom;
$R_2$ has one of the values defined for (I);
$R_3$ represents a methyl group;
$R_4$ and $R_5$ represent a 2,4-dichlorophenyl and a 4-chlorophenyl, a 2,4-dichlorophenyl and a 4-bromophenyl, a 2-chlorophenyl and a 4-chlorophenyl, or a 2,4-dichlorophenyl and a 4-methoxyphenyl;
X represents a group —CO—; —$SO_2$— or —$CON(R_6)$—;

and also the hydrates thereof or solvates thereof.

Preference is most particularly given to the compounds of formula (I) in which the substituents $R_1$, $R_3$, $R_4$, $R_5$ and X are as defined above and $R_2$ represents a group chosen from:
- a 3-chlorophenyl, a 3-trifluoromethylphenyl, a 4-trifluoromethylphenyl and a hept-4-yl;

and also the hydrates thereof or solvates thereof.

In accordance with the invention, the compounds of formula (I) can be prepared according to a method which is characterized in that:

a compound of formula:

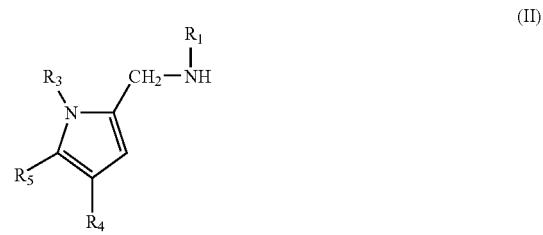

in which $R_1$, $R_3$, $R_4$ and $R_5$ are as defined for a compound of formula (I), is treated:

either with an acid or a functional derivative of this acid of formula

$$HOOC-R_2 \quad (III)$$

in which $R_2$ is as defined for a compound of formula (I), when a compound of formula (I) in which —X— represents a —CO— group must be prepared or with a sulfonyl halide of formula:

$$Hal-SO_2-R_2 \quad (IV)$$

in which $R_2$ is as defined for a compound of formula (I) and Hal represents a halogen atom, preferably chlorine, when a compound of formula (IB) in which —X— represents an —SO$_2$— group must be prepared;

or with a haloformate of formula:

$$HalCOOAr \quad (V)$$

in which Hal represents a halogen atom and Ar represents a phenyl or a 4-nitrophenyl, so as to obtain an intermediate compound of formula:

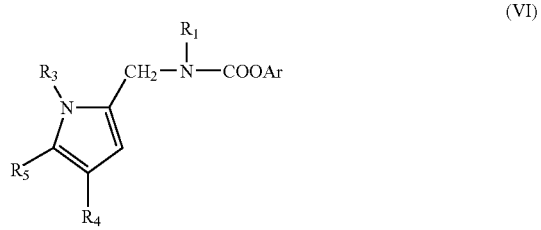

(VI)

in which $R_1$, $R_3$, $R_4$ and $R_5$ are as defined for a compound of formula (I), which is subsequently reacted with an amine of formula:

$$HN(R_6)R_2 \quad (VII)$$

in which $R_2$ and $R_6$ are as defined for a compound of formula (I), when a compound of formula (IC) in which —X— represents a —CON($R_6$)— group must be prepared;

or with an isothiocyanate of formula $R_2$—N=C=S (IX) in which $R_2$ is as defined for a compound of formula (I), when a compound of formula (ID) in which —X— represents a —CSN($R_6$)— group must be prepared.

Optionally, the compound of formula (I) is converted into one of its addition salts with an acid.

When a compound of formula (II) is treated with the acid of formula (III) itself, the process is carried out in the presence of a coupling agent used in peptide chemistry, such as 1,3-dicyclohexylcarbodiimide (DCC) or benzotriazol-1-yloxytris(dimethylamino)phosphonium hexafluorophosphate (BOP) or benzotriazol-1-yloxytris(pyrrolidino)phosphonium hexafluorophosphate (PyBOP) or 2-(1H-benzotriazol-1-yl)-1,1,3,3-tetra-methyluronium tetrafluoroborate (TBTU), in the presence of a base such as triethylamine, N,N-diisopropy-lethylamine or 4-dimethylaminopyridine, in a solvent such as dichloromethane, dichloroethane, N,N-dimethylformamide or tetrahydrofuran, at a temperature of between −10° C. and the reflux temperature of the solvent.

As functional derivative of the acid (III), use may be made of the acid chloride, the anhydride, a mixed anhydride, a $C_1$-$C_4$ alkyl ester in which the alkyl is straight or branched, or an activated ester, for example the p-nitrophenyl ester.

Thus, in the method according to the invention, the acid chloride obtained by reaction of thionyl chloride or of oxalyl chloride with the acid of formula (III) can also be reacted with the compound of formula (II), in a solvent, such as a chlorinated solvent (dichloromethane, dichloroethane or chloroform, for example), an ether (tetrahydrofuran or dioxane, for example) or an amide (N,N-dimethylformamide, for example), under an inert atmosphere, at a temperature of between 0° C. and ambient temperature, in the presence of a tertiary amine such as triethylamine, N-methylmorpholine or pyridine.

A variant consists in preparing the mixed anhydride of the acid of formula (III) by reacting ethyl chloroformate with the acid of formula (III), in the presence of a base such as triethylamine, and in reacting it with the compound of formula (II), in a solvent such as dichloromethane, under an inert atmosphere, at ambient temperature, in the presence of a base such as triethylamine.

When a compound of formula (II) is treated with a sulfonyl halide of formula (IV), the process is carried out in the presence of a base such as triethylamine or diisopropylethylamine, in a solvent such as dichloromethane or tetrahydrofuran, and at a temperature of between ambient temperature and the reflux temperature of the solvent.

When a compound of formula (II) is treated with a haloformate of formula (V), the process is carried out in the presence of a base such as triethylamine, in a solvent such as dichloromethane, and at a temperature of between 0° C. and ambient temperature. The intermediate compound of formula (VI) thus obtained is then reacted with an amine of formula (VII), in a solvent such as dichloromethane, in the presence of a base such as triethylamine, and at a temperature of between 0° C. and the reflux temperature of the solvent.

According to a variant of the method, the compounds of formula (IC) in which —X— represents a —CON($R_6$)— group in which $R_6$=H are compared by reacting a compound of formula (II) with an isocyanate of formula $R_2$—N=C=O (VIII), in the presence of a base such as triethylamine, in a solvent such as dichloromethane, and at a temperature of between ambient temperature and the reflux temperature of the solvent.

According to another variant of the method, the compounds of formula (IC) in which —X— represents a —CON ($R_6$)— group are prepared by reacting a compound of formula (II) with a compound of formula ClCON($R_6$)$R_2$ (IX) in the presence of a base such as triethylamine, in a solvent such as dichloromethane, and at a temperature of between 0° C. and ambient temperature.

The compounds of formula (I) in which $R^1$ represents a ($C_1$-$C_3$)alkyl can also be prepared from the corresponding compounds of formula (I) in which $R_1$ represents a hydrogen atom, by a method chosen from the methods known to those skilled in the art. Among these, mention may be made of alkylation with an alkyl halide, reductive amination with an aldehyde in a reducing medium, or alternatively acylation with an acyl chloride, followed by reduction.

The compounds of formula (I) thus obtained can be subsequently separated from the reaction medium and purified according to conventional methods, for example by crystallization or chromatography.

The compounds of formula (II) can be prepared according to the following reaction scheme:

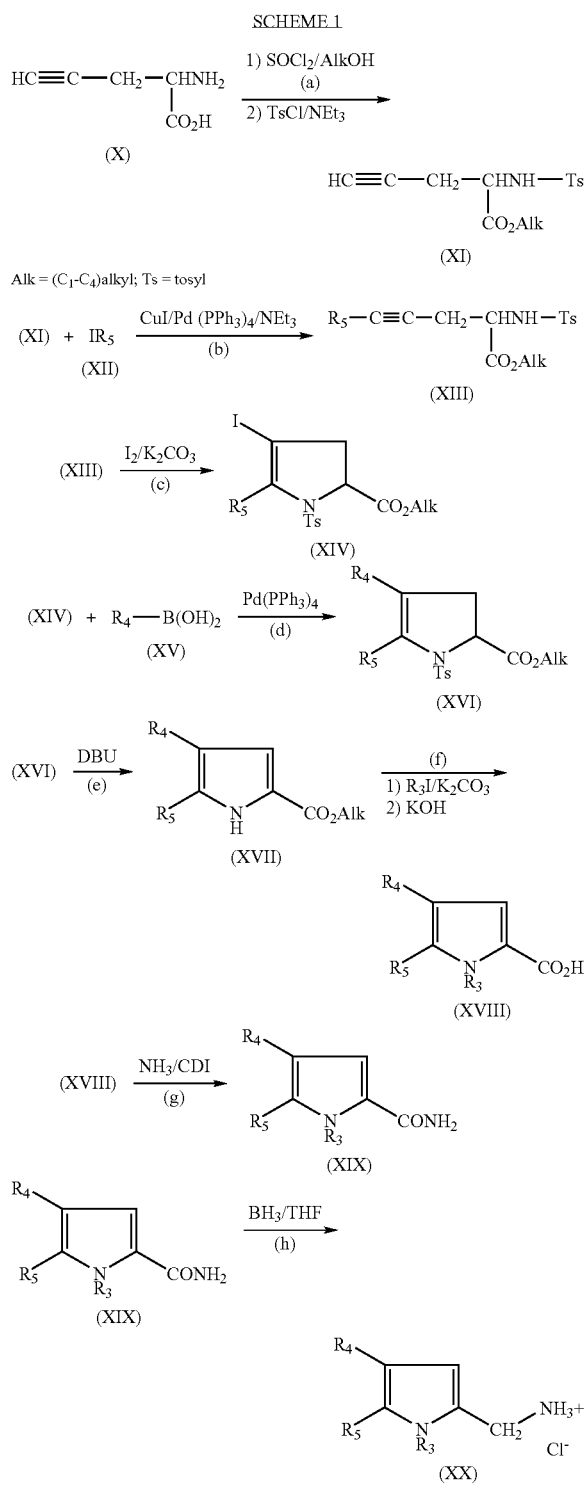

The preparation of the dihydropyrrole derivative of formula (XIV) by means of steps a), b) and c) is carried out according to J. Chem. Soc. Perkin Trans. 1, 2002, 622-628.

The compounds of formula (III) are known.

The compounds of formula (IV) are commercially available or described in the literature, or can be prepared according to methods which are described therein, such as in J. Org. Chem. USSR, 1970, 6, 2454-2458; J. Am. Chem. Soc., 1952, 74, 2008; J. Med. Chem., 1977, 20(10), 1235-1239; EP0469 984; WO 95/18105.

For example, the compounds of formula (IV) can be prepared by halogenation of the corresponding sulfonic acids or of their salts, for example of their sodium or potassium salts. The reaction is carried out in the presence of an halogenating agent such as phosphorus oxychloride, thionyl chloride, phosphorus trichloride, phosphorus tribromide or phosphorus pentachloride, without solvent or in a solvent such as a halogenated hydrocarbon or N,N-dimethylformamide and a temperature of between −10° C. and 200° C.

The substitution of the dihydropyrrole nucleus with a substituted phenyl group ($R_4$) is carried out in step d) by the action of a substituted phenylboronic acid of formula (XV) in the presence of a palladium catalyst such as tetrakis(triphenylphosphine) [Pd(PPh$_3$)$_4$], bis(dibenzylideneacetone)palladium(0) [Pd(dba)$_2$], tris(dibenzylideneacetone)dipalladium(0), palladium acetate Pd(II) [Pd(OCOCH$_3$)$_2$] or dichloro(diphenyl-phosphinoferrocene)Pd(II) [PdCl$_2$dppf], and in the presence of a base.

In step e), the protection of the nitrogen with the tosyl group is removed by the action of a diamine such as DBU (1,8-diazabicyclo[5.4.0]undecene) and the pyrrole nucleus is simultaneously aromatized.

In step f), the nitrogen of the pyrrole is alkylated by the action of an alkyl iodide of formula $R_3I$, and then the ester is hydrolyzed in a basic medium so as to obtain, after acidification, the acid of formula (XVIII).

In step (g), the acid of formula (XVIII) is treated with gaseous ammonia in an aprotic polar solvent, such as DMF or acetonitrile, in the presence of a coupling agent such as CDI (1,1'-carbonyl bis(1H-imidazole), 1,3-dicyclohexylcarbodiimide (DCC), benzotriazol-1-yloxytris(dimethylamino) phosphonium (BOP) hexafluoro-phosphate or benzotriazol-1-yloxy-tris(pyrrolidino)phosphonium (PyBOP) hexafluorophosphate.

In step (h), the reduction of the carboxamide function of the compound of formula (XIX) is carried out by means of a reducing agent such as borane or lithium aluminum hydride, in a solvent such as tetrahydrofuran or isopropyl ether, at a temperature of between ambient temperature and the reflux temperature of the solvent, followed by an acid hydrolysis.

The compounds of formula (II) are new. Thus, a subject of the present invention is also the compounds of formula:

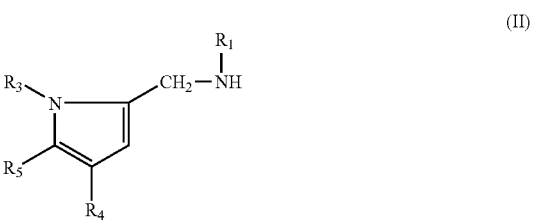

in which $R_1$, $R_3$, $R_4$ and $R_5$ are as defined for (I).

More particularly, a subject of the present invention is the compounds of formula (II) in which:
 $R_1$=H;
 $R_3$=Me;
 $R_4$=2,4-dichlorophenyl or 2-chlorophenyl;
 $R_5$=4-chlorophenyl, 4-bromophenyl or 4-methoxy-phenyl.

The following EXAMPLES describe the preparation of certain compounds in accordance with the invention. These examples are not limiting and merely illustrate the present invention. The numbers of the compounds exemplified refer to those given in table I hereinafter, which illustrates the chemical structures and the physical properties of some compounds according to the invention.

In the preparations and in the examples, the following abbreviations are used:
ether: diethyl ether
iso ether: diisopropyl ether
DMSO: dimethyl sulfoxide
DMF: N,N-dimethylformamide
THF: tetrahydrofuran
TBTU: 2-(1H-benzotriazol-1-yl)-1,1,3,3-tetramethyl-luronium tetrafluoroborate
DCM: dichloromethane
EtOAc: ethyl acetate
DIPEA: diisopropylethylamine
$BH_3$-THF: borane-tetrahydrofuran complex
DBU: 1,8-diazabicyclo[5,4,0]undec-7-ene
TFA: trifluoroacetic acid
2N hydrochloric ether: 2N solution of hydrochloric acid in diethyl ether
Mp: melting point
AT: ambient temperature
Bp: boiling point
HPLC: high performance liquid chromatography
Silica H: 60H silica gel sold by Merck (DARMSTAD)
Buffer solution pH=2: solution of 16.66 g of $KHSO_4$ and 32.32 g of $K_2SO_4$ in 1 liter of water.

The proton nuclear magnetic resonance ($^1$H NMR) spectra are recorded at 200 MHz in DMSO-$d_6$. The chemical shifts δ are expressed in parts per million (ppm). For the interpretation of the spectra, the following abbreviations are used: s: singlet, d: doublet, t: triplet, q: quadruplet, up: unresolved peak, mt: multiplet, bs: broad singlet, rd: resolved doublet.

The compounds according to the invention are analyzed by LC/UV/MS (liquid chromatography/UV detection/mass spectrometry) coupling. The molecular peak (MH$^+$) and the retention time (tr) in minutes are measured.

Conditions A:
A Symmetry C18 column of 2.1×50 mm, 3.5 μm, is used at 30° C., flow rate 0.4 ml/minute.
The eluent is composed as follows:
solvent A: 0.005% of trifluoroacetic acid (TFA) in water at pH 3.15;
solvent B: 0.005% of TFA in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ 210 nm and the mass detection is carried out in the positive ESI (electro spray ionization) chemical ionization mode.

Conditions MS2
An XTERRA MS C18 column of 2.1×30 mm, 3.5 μm, is used at a flow rate of 0.8 ml/minute.

The eluent is composed as follows:
Solvent A: 0.025% of TFA in water,
Solvent B: 0.025% of TFA in acetonitrile.
Gradient

| Time (min) | % A | % B |
|---|---|---|
| 0 | 100 | 0 |
| 2 | 0 | 100 |
| 2.7 | 0 | 100 |
| 2.75 | 100 | 0 |

The UV detection is carried out with a diode array detector between 210 and 400 nm and the mass detection is carried out in the positive ESI mode.

PREPARATIONS

Preparation 1

A) Methyl 2-(((4-methylphenyl)sulfonyl)amino)pent-3-ynoate 2.5 g of 2-aminobut-3-ynoic acid are suspended in 45 ml of methanol at 0° C. 1.8 ml of thionyl chloride are run in dropwise at this temperature and the mixture is then refluxed for 3 hours. The solution is concentrated and the residue is dried under reduced pressure. The latter is solubilized in 60 ml of acetonitrile followed by 5.4 ml of triethylamine and then 4.6 g of tosyl chloride are added. The mixture is stirred at ambient temperature for 19 hours and then at 50° C. for a further one hour. After concentration, the crude product is solubilized in dichloromethane and the organic phase is washed successively with a saturated aqueous solution of $KHSO_4$ and then of $K_2CO_3$. The organic phase is dried over magnesium sulfate and then filtered and, finally, concentrated so as to obtain 5.18 g of the expected compound.
$^1$H NMR: δ (ppm): 2.35: s: 3H, 2.45: up: 2H, 3.45: s: 3H, 3.9: rd: 1H; 7.35: d: 2H, 7.65: d: 2H, 8.4: d: 1H.

B) Methyl 5-(4-chlorophenyl)-2-(4-tosylamino)pent-4-ynoate 1 g of the compound from the preceding step and 0.57 g of 4-chloroiodobenzene are solubilized in 20 ml of anhydrous DMF. The solution is degassed under vacuum for 30 minutes. 0.64 ml of triethylamine and then 0.28 g of tetrakis(triphenylphosphine)palladium(0) and 0.1 g of copper iodide are added. The mixture is stirred at ambient temperature under an argon atmosphere for 19 hours. The reaction mixture is concentrated and purified by silica gel chromatography, elution being carried out with cyclohexane/ethyl acetate (80/20; v/v). 1 g of the expected compound is recovered.
$^1$H NMR: δ (ppm): 2.35: s: 3H, 2.70-2.80: up: 2H, 3.45: s: 3H, 4.05: rd: 1H; 7.35: m: 4H, 7.4: d: 2H, 7.65: d: 2H, 8.51: d: 1H.

C) Methyl 5-(4-chlorophenyl-4-iodo-1-(4-tosyl-sulfonyl)-2,3-dihydro-1H-pyrrole-2-carboxylate 1 g of the compound obtained in the preceding step is dissolved in 5 ml of anhydrous acetonitrile in the presence of 1 g of potassium carbonate at 0° C. 2 g of solid iodine are added, in several small fractions, at this temperature and with stirring. The mixture is allowed to return to ambient temperature for 24 hours. The reaction is stopped by adding a solution of sodium thiosulfate until discoloration occurs, and the organic phase is extracted with dichloromethane. After drying over the magnesium sulfate, filtration and concentration, 1.27 g of the expected compound are obtained.

LC/MS: M=517, tr=10.8 minutes.

D) Methyl 5-(4-chlorophenyl)-4-(2,4-dichlorophenyl)-1-tosylsulfonyl-2,3-dihydro-1H-pyrrole-2-carboxylate 15 g of the compound obtained in the preceding step and 6.8 g of 2,4-dichlorophenylboronic acid are solubilized in a mixture of 150 ml of methanol and 710 ml of toluene, in the presence of 48 ml of a solution of sodium carbonate (2N). The reaction medium is left under argon for 30 minutes and then 4.7 g of tetrakis(triphenylphosphine)palladium(0) are added. The solution is heated at 60° C. for 4 hours under an inert atmosphere. After cooling, the crude product is concentrated and purified by silica gel chromatography in toluene. 9.7 g of the expected compound are obtained in the form of a white powder.

$^1$H NMR: δ (ppm): 2.4: s: 3H, 2.75-2.95: up: 1H; 3.8: s: 3H, 5.15: d: 1H; 6.7: d: 1H; 7.1-7.7: up: 6H.

E) Methyl 5-(4-chlorophenyl)-4-(2,4-dichlorophenyl)-1H-pyrrole-2-carboxylate 9.7 g of the compound obtained in the preceding step are solubilized in 60 ml of anhydrous N,N-dimethylformamide. 5.4 ml of DBU are then added and the mixture is heated at 100° C. for 24 hours. The crude product is concentrated and then, after the addition of ethanol, a white precipitate appears. The latter is filtered off, and 6 g of the expected compound are recovered.

$^1$H NMR: δ (ppm): 3.8: s: 3H, 6.9: s: 1H; 7.2: s: 1H; 7.25: s: 2H, 7.3-7.4: up: 3H, 7.65: rd: 1H; 12.4: s: 1H.

F) 5-(4-chlorophenyl)-4-(2,4-dichorophenyl)-1-methyl-1H-pyrrole-2-carboxylic acid 5.9 g of the compound obtained in the preceding step are solubilized in 150 ml of DMF and 3.5 g of potassium carbonate are added. At ambient temperature, 1.5 ml of iodomethane are added to the mixture and the whole is left to stir at AT for 24 hours. The solution is filtered and the filtrate is evaporated to dryness and then solubilized in 430 ml of methanol, and 7 ml of water are added followed by 8.7 g of potassium hydroxide pellets. The mixture is refluxed for 24 hours. After concentration, the solid obtained is washed with ether and then dissolved in dichloromethane. The organic phase is treated with a 10% aqueous solution of hydrochloric acid. The organic phase is then dried over magnesium sulfate and then filtered and concentrated. 5.8 g of the expected compound are recovered in the form of a white solid, Mp=194° C.

$^1$H NMR: δ (ppm): 3.75: s: 3H, 6.9: s: 2H, 7.05: rd: 2H, 7.15-7.30: up: 3H, 7.45: d: 2H, 7.55: rd: 1H, 12.5: s: 1H.

G) 5-(4-chlorophenyl)-4-(2,4-dichlorophenyl)-1-methyl-1H-pyrrole-2-carboxamide 4 g of acid obtained in the preceding step and 1.9 g of 1,1'-carbonylbis (1H-imidazole) are solubilized in 40 ml of anhydrous DMF. The mixture is stirred for 1 hour at AT and the solution is then sparged with ammonia gas for 1 hour. After the addition of water, the product is extracted with ethyl ether. The organic phase is washed with a solution of NaOH (1N). After drying over MgSO$_4$, filtration and concentration, 3.3 g of a white solid corresponding to the expected amide are obtained.

LC/MS: conditions 1, MH$^+$=379, tr=10.42. Purity: 95.2%.

H) [5-(4-chlorophenyl)-4-(2,4-dichlorophenyl)-1-methyl-1H-pyrrol-2-yl]methanaminium chloride 43 ml of a solution of [BH$_3$OTHF] (1N) are added dropwise to 8 ml of a solution of 3.2 g of the compound obtained in the preceding step in THF. The mixture is then heated at 60-70° C. for 19 hours. After cooling to 0° C., 15 ml of methanol are added. The mixture is concentrated by three quarters and the remaining liquor is added dropwise to 200 ml of a solution of hydrochloric ether. After precipitation and filtration, 2.55 g of the expected compound are obtained in the form of a white solid.

$^1$H NMR: 2.1 ppm: s: 3H, 3.9 ppm: s: 2H, 6.55 ppm: s: 1H; 7.05-7.55 ppm: up: 7H, 8.35 ppm: s: 3H.

LC/MS: MH$^+$=364, tr=9.04.

EXAMPLE 1

Compound No. 1

N-((5-(4-chlorophenyl)-4-(2,4-dichlorophenyl)-1-methyl-1H-pyrrol-2-yl)methyl)-4-(trifluoromethyl)benzamide 1 g of the compound of preparation 1 is solubilized in 30 ml of DCM, in the presence of 1 ml of triethylamine. 0.57 ml of 4-trifluoromethylbenzoyl chloride is added and the mixture is stirred for 24 hours at AT. The resulting mixture is evaporated to dryness and then purified by chromatography to give 0.42 g of the expected compound in the form of a solid.

EXAMPLE 2

Compound No. 2

3-chloro-N-((5-4-chlorophenyl)-4-(2,4-dichlorophenyl)-1-methyl-1H-pyrrol-2-yl)methyl)benzenesulfonamide 0.5 g of the compound of preparation 1 is dissolved in 15 ml of DCM in the presence of 0.4 ml of triethylamine; 0.32 mg of 3-chlorobenzenesulfonyl chloride is added and the mixture is left to stir at AT for 20 hours. The resulting mixture is evaporated to dryness and then purified by chromatography to give 0.15 g of the expected compound in the form of a solid.

EXAMPLE 3

Compound No. 5

N-((5-(4-chlorophenyl-4-(2,4-dichlorophenyl)-1-methyl-1H-pyrrol-2-yl)methyl)-N'-(3-(trifluoromethyl)phenyl)urea 0.8 g of the compound of preparation 1 is solubilized in 40 ml of DCM in the presence of 0.40 ml of triethylamine; 0.34 ml of 3-trifluoromethylbenzene isocyanate is added and the mixture is left to stir at AT for 20 hours. The resulting mixture is purified by chromatography to give 0.25 g of the expected compound in the form of a solid.

EXAMPLE 4

Compound Nos 6 to 18

The compounds of formula (IA) are prepared by combinatory chemistry according to the method described below:

Carboxylic acids of formula (III) are dissolved in DMF to a concentration of 0.25M in the presence of 3 equivalents of DIPEA. 120 μl of this solution are placed in each 2 ml well, as are 120 μl of a solution of TBTU in DMF at a concentration of 0.25M. 300 μl of a solution containing methylamine in DMF at a concentration of 0.1M and 3 equivalents of DIPEA are added to each well. The plates are shaken at AT for 16 hours and then evaporated. The products formed in each well are dissolved with 500 μl of EtOAc, 400 μl of 0.1M $Na_2CO_3$ are added, and the plates are shaken. After separation of the phases by settling, 430 μl of aqueous phase are discarded, 300 μl of 5% NaCl are then added and the plates are shaken. 350 μl of aqueous phase are then discarded and the residues are analyzed by LC/UV/MS.

The table which follows illustrates the chemical structures and the physical properties of the compounds according to the invention. In this table, Me, Et, Pr and tBu represent, respectively, methyl, ethyl, propyl and tert-butyl groups.

TABLE 1

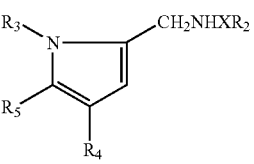

| Compound No. | X | $R_2$ | $R_3$ | $R_4$ | $R_5$ | Characterization/ Conditions |
|---|---|---|---|---|---|---|
| 1 | —CO— | 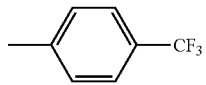 | Me | 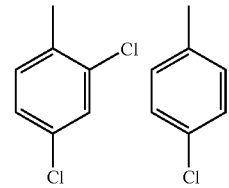 | 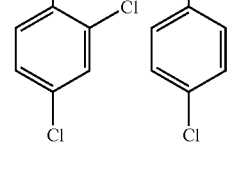 | Mp = 82° C.<br>$MH^+$ = 537<br>tr = 12.27<br>A |
| 2 | —$SO_2$— | 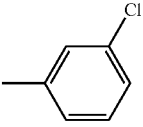 | Me | 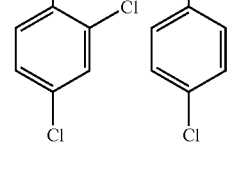 | 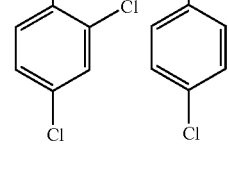 | Mp = 70° C.<br>$MH^+$ = 537<br>tr = 11.86<br>A |
| 3 | —$SO_2$— | 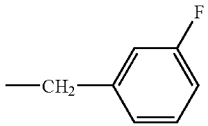 | Me | 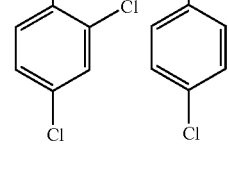 | 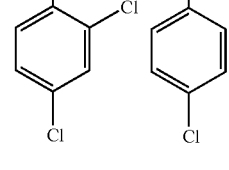 | Mp = 80° C.<br>$MH^+$ = 537<br>tr = 12.03<br>A |
| 4 | —SO2— | 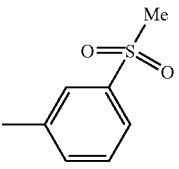 | Me | 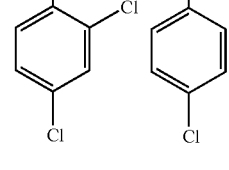 | 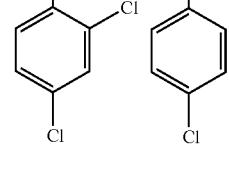 | Mp = 106° C.<br>$MH^+$ = 583<br>tr = 11.19<br>A |
| 5 | —CONH— | 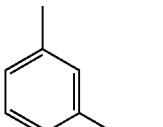 | Me | 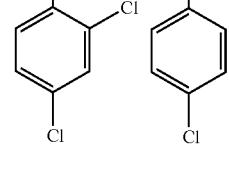 |  | Mp = 105° C.<br>$MH^+$ = 552<br>tr = 12.23<br>A |

TABLE 1-continued

Structure: R3-N (pyrrole), with CH2NHXR2 at position 2, R4 at position 3, R5 at position 5.

| Compound No. | X | R₂ | R₃ | R₄ | R₅ | Characterization/ Conditions |
|---|---|---|---|---|---|---|
| 6 | —CO— | 1-methylcyclohexyl | Me | 2,4-diCl-phenyl | 4-Cl-phenyl | MH⁺ = 489.6; tr = 2.12; MS2 |
| 7 | —CO— | cyclopentyl | Me | 2,4-diCl-phenyl | 4-Cl-phenyl | MH⁺ = 461.5; tr = 2.03; MS2 |
| 8 | —CO— | endo-norbornyl (racemic) | Me | 2,4-diCl-phenyl | 4-Cl-phenyl | MH⁺ = 487.6; tr = 2.10; MS2 |
| 9 | —CO— | CH(Pr)(Pr) | Me | 2,4-diCl-phenyl | 4-Cl-phenyl | MH⁺ = 491.6; tr = 2.13; MS2 |
| 10 | —CO— | cyclohexyl | Me | 2,4-diCl-phenyl | 4-Cl-phenyl | MH⁺ = 475.6; tr = 2.06; MS2 |
| 11 | —CO— | 4-(pyrrol-1-yl)phenyl | Me | 2,4-diCl-phenyl | 4-Cl-phenyl | MH⁺ = 534.5; tr = 2.12; MS2 |
| 12 | —CO— | 4-tBu-phenyl | Me | 2,4-diCl-phenyl | 4-Cl-phenyl | MH⁺ = 525.6; tr = 2.19; MS2 |

TABLE 1-continued

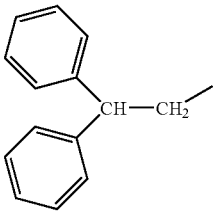

| Compound No. | X | R₂ | R₃ | R₄ | R₅ | Characterization/ Conditions |
|---|---|---|---|---|---|---|
| 13 | —CO— | 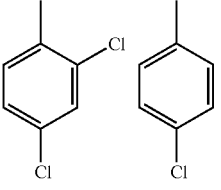 | Me | 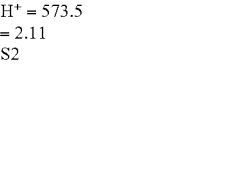 | 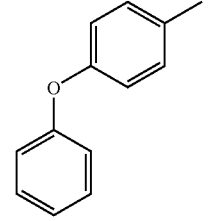 | $MH^+ = 573.5$<br>tr = 2.11<br>MS2 |
| 14 | —CO— | 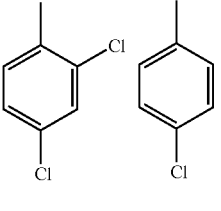 | Me | 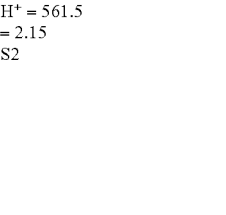 | 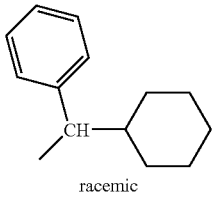 | $MH^+ = 561.5$<br>tr = 2.15<br>MS2 |
| 15 | —CO— | 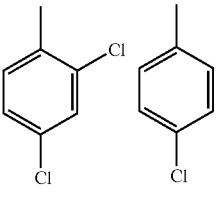<br>racemic | Me | 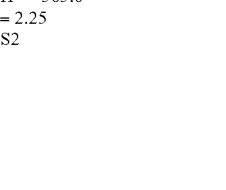 | 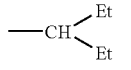 | $MH^+ = 565.6$<br>tr = 2.25<br>MS2 |
| 16 | CO— | 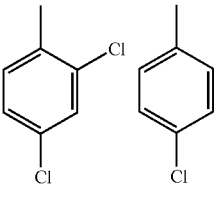 | Me | 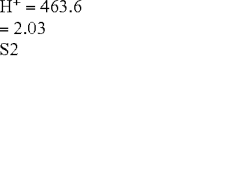 | 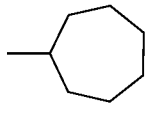 | $MH^+ = 463.6$<br>tr = 2.03<br>MS2 |
| 17 | —CO— | 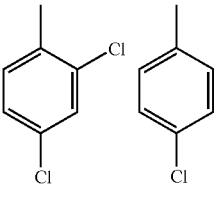 | Me | 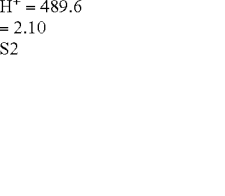 | 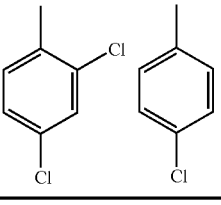 | $MH^+ = 489.6$<br>tr = 2.10<br>MS2 |
| 18 | —CO— | -tBu | Me | 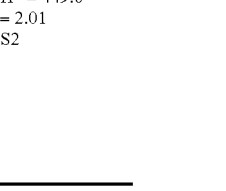 | | $MH^+ = 449.6$<br>tr = 2.01<br>MS2 |

The compounds of formula (I) show very good in vitro affinity ($IC_{50} \leq 5 \times 10^{-7}$ M) for cannabinoid $CB_1$ receptors, under the experimental conditions described by M. Rinaldi-Carmona et al. (FEBS Letters, 1994, 350, 240-244).

The antagonist nature of the compounds of formula (I) was demonstrated by the results obtained in models of inhibition of adenylate cyclase as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The interaction of a compound according to the invention with the CB1 receptors present in the brain is determined in mice by means of the ex vivo test for binding of [3H]-CP55940 after intravenous injection, as described in Rinaldi-Carmona M et al. FEBS Letters (1994), 350, 240-244 and Rinaldi-Carmona M et al., Life Sciences (1995), 56, 1941-1947.

The interaction of a compound according to the invention with the CB1 receptors present peripherally is determined in mice by means of the test for reversion of the inhibitory effect of CP55940 on gastrointestinal transit after oral administration, as described in Rinaldi-Carmona M. et al., JPET (2004), 310, 905-914.

The toxicity of the compounds of formula (I) is compatible with their use as medicaments.

Thus, according to another of its aspects, a subject of the invention is medicaments for human or veterinary medicine, which comprise a compound of formula (I), or an addition salt thereof with a pharmaceutically acceptable acid, or alternatively a solvate or a hydrate of the compound of formula (I).

Thus, the compounds according to the invention can be used in the treatment or prevention of diseases involving cannabinoid $CB_1$ receptors, in humans or in animals, in particular in mammals, including, in a non-limiting manner, dogs, cats, horses, cattle and sheep.

For example, and in a nonlimiting manner, the compounds of formula (I) are of use as psychotropic medicaments, in particular for the treatment of psychiatric disorders including anxiety, depression, mood disorders, insomnia, delirium disorders, obsessive disorders, psychoses in general, schizophrenia, attention deficit hyperactivity disorders (ADHD) in hyperkinetic children, and also for the treatment of disorders associated with the use of psychotropic substances, in particular in the case of a substance abuse and/or dependency on a substance, including alcohol dependency and nicotine dependency.

The compounds of formula (I) according to the invention can be used as medicaments for the treatment of migraine, stress, diseases of psychosomatic origin, panic attacks, epilepsy, motor disorders, in particular dyskinesia or Parkinson's disease, shaking and dystonia.

The compounds of formula (I) according to the invention can also be used as medicaments in the treatment of memory disorders, cognitive disorders, in particular in the treatment of senile dementia and Alzheimer's disease, and also in the treatment of attention or consciousness disorders. Furthermore, the compounds of formula (I) can be used as neuroprotective agents, in the treatment of ischemia, cranial trauma and the treatment of acute or chronic neurodegenerative diseases: including chorea, Huntington's chorea and Tourette's syndrome.

The compounds of formula (I) according to the invention can be used as medicaments in the treatment of pain: neuropathic pain, acute peripheral pain, chronic pain of inflammatory origin or pain induced by an anticancer treatment.

The compounds of formula (I) according to the invention can be used as medicaments in human or veterinary medicine, in the treatment and prevention of appetite disorders, appetence disorders (for sugars, carbohydrates, drugs, alcohols or any appetizing substance) and/or eating disorders, in particular for the treatment of obesity or bulimia and also for the treatment of type II diabetes or non-insulin-dependent diabetes and for the treatment of dyslipidemia and metabolic syndrome. Thus, the compounds of formula (I) according to the invention are of use for the treatment and prevention of obesity and the risks associated with obesity, in particular cardiovascular risks.

Furthermore, the compounds of formula (I) according to the invention can be used as medicaments in the treatment and prevention of gastrointestinal disorders, diarrhea disorders, ulcers, vomiting, blood urinary disorders, liver diseases such as chronic cirrhosis, fibrosis, hepatic steatosis, steatohepatitis; and also disorders of endocrine origin, cardiovascular disorders, hypotension, atherosclerosis, hemorrhagic shock, septic shock, asthma, chronic bronchitis, chronic obstructive pulmonary diseases, Raynaud's syndrome, glaucoma, fertility disorders, preterm labor, inflammatory phenomena, immune system diseases, in particular autoimmune diseases and neuroinflammatory diseases such as rheumatoid arthritis, rectional arthritis, diseases resulting in demyelinization, multiple sclerosis, infectious and viral diseases such as encephalitis, cerebral strokes, and also as medicaments for anticancer chemotherapy, for the treatment of Guillain-Barré syndrome and for the treatment of bone diseases and osteoporosis.

According to the present invention, the compounds of formula (I) are of most particular use for the preparation of medicaments for use in the prevention and treatment of psychotic disorders, in particular schizophrenia, attention deficit hyperactivity disorders (ADHD) in hyperkinetic children; memory and cognitive deficits; alcohol dependency, nicotine dependency, alcohol withdrawal and tobacco withdrawal, and acute or chronic neurodegenerative diseases.

More particularly, the compounds of formula (I) according to the present invention are of use in the treatment and prevention of appetite disorders, metabolic disorders, gastrointestinal disorders, inflammatory phenomena, immune system diseases, psychotic disorders, alcohol dependency and nicotine dependency.

According to one of its aspects, the present invention relates to the use of a compound of formula (I), pharmaceutically acceptable salts thereof and solvates or hydrates thereof, for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a solvate or hydrate of said compound, and also at least one pharmaceutically acceptable excipient.

Said excipients are chosen according to the pharmaceutical form and the method of administration desired, from the usual excipients known to those skilled in the art.

The pharmaceutical compositions according to the present invention may contain, along with a compound of formula (I), one (or more) other active ingredient that is of use in the treatment of the disorders and diseases indicated above.

Thus, a subject of the present invention is also pharmaceutical compositions containing a compound of formula (I) according to the present invention combined with one (or more) active ingredient chosen from one of the following therapeutic classes:

another cannabinoid $CB_1$ receptor antagonist;
a cannabinoid $CB_2$ receptor modulator;
an angiotensin II $AT_1$ receptor antagonist;
a converting enzyme inhibitor;
a calcium antagonist;
a diuretic;

a beta-blocker;

an antihyperlipemia agent or an antihypercholesterolemia agent;

an antidiabetic;

another anti-obesity agent;

a nicotine agonist or a partial nicotine agonist;

an antidepressant, an antipsychotic or an axiolytic;

an anticancer agent or an antiproliferative agent;

an opioid antagonist;

and also:

a memory-improving agent;

an agent for use in the treatment of alcoholism or withdrawal symptoms;

an agent of use for treating osteoporosis;

a nonsteroidal or steroidal anti-inflammatory;

an anti-infective;

an analgesic;

an antihistamine.

The expression "angiotensin II AT$_1$ receptor antagonist" is intended to mean a compound such as candesartan, cilexitil, eprosartan, irbesartan, losartan potassium, olmesartan medoxomil, telmisartan or valsartan, each of these compounds themselves possibly being combined with a diuretic such as hydrochlorothiazide.

The term "converting enzyme inhibitor" is intended to mean a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, each of these compounds itself possibly being combined with a diuretic such as hydrochlorothiazide or indampamide, or with a calcium antagonist such as amlodipine, diltiazem, felodipine or verapamil.

The term "calcium antagonist" is intended to mean a compound such as amlodipine, aranidipine, benidipine, bepridil, cilnidipine, diltiazem, efonidipine hydrochloric ethanol, fasudil, felodipine, isradipine, lacidipine, lercanidipine hydrochloride, manidipine, mibrefradil hydrochloride, nicardipine, nifedipine, nilvadipine, nimodipine, nisoldipine, nitrendipine, terodiline or verapamil.

The term "beta-blocker" is intended to mean a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertatolol, tilisolol, timolol, xamoterol or xibenolol.

The term "antihyperlipidemic agent" or "antihypercholesterolemia agent" is intended to mean a compound chosen from fibrates such as alufibrate, beclobrate, bezafibrate, ciprofibrate, clinofibrate, clofibrate, etofibrate or fenofibrate; statins (HMG-CoA reductase inhibitors), such as atorvastatin, fluvastatin sodium, lovastatin, pravastatin, rosuvastatin or simvastatin, or a compound such as acipimox, aluminum nicotinate, azacosterol, cholestyramine, dextrothyroxine, meglutol, niceritrol, nicoclonate, nicotinic acid, beta-sitosterol or tiadenol.

The term "antidiabetic" is intended to mean a compound belonging to one of the following classes: sulfonylureas, biguanidines, alpha-glucosidase inhibitors, thiazolidinediones, metiglinides, such as acarbose, acetohexamide, carbutamide, chlorpropamide, glibenclamide, glibornuride, gliclazide, glimerpiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose, and also insulin and insulin analogs.

The term "another anti-obesity agent" is intended to mean a compound such as amfepramone, benfluorex, benzphetamine, indanorex, mazindole, mefenorex, methamphetamine, D-norpseudoephedrine, sibutramine, a topiramate, a lipase inhibitor (orlistat or cetilistat), a PPAR agonist (peroxisome proliferator activated receptor agonist), a dopamine agonist, a leptin receptor agonist, a serotonin reuptake inhibitor, a beta-3 agonist, a CCK-A agonist, an NPY inhibitor, an MC4 receptor agonist, an MCH (Melanine Concentrating Hormone) receptor antagonist, an orexin agonist, a phosphodiesterase inhibitor, an 11βHSD (11-β-hydroxy steroid dehydrogenase) inhibitor, a DPP-IV (dipeptidyl peptidase IV) inhibitor, a histamine H3 agonist (or inverse agonist), a CNTF (Ciliary Neurotrophic Factor) derivative, a GHS (Growth Hormone Secretagogue) receptor agonist, a ghrelin modulator, a diacylglycerol acyltransferase (DGAT) inhibitor, a phosphodiesterase (PDE) inhibitor, a thyroid hormone antagonist, a glucocorticoid receptor antagonist, a stearoyl-Co-A-desaturase (SCD) inhibitor, a phosphate, glucose, fatty acid or dicarboxylate transport inhibitor, a 5HT$_2$ antagonist, a 5HT$_6$ antagonist or a bombesin agonist.

The term "opioid antagonist" is intended to mean a compound such as naltrexone, naloxone or nalmefene.

The expression "agent for use in the treatment of alcoholism and withdrawal symptoms" is intended to mean acamprosate, benzodiazepines, beta-blockers, clonidine and carbamazepine.

The expression "agent of use for treating osteoporosis" is intended to mean, for example, bisphosphonates such as etidronate, clodronate, tiludronate or risedronate.

According to the present invention, other compounds with antihyperlipidemia, antihypercholesterolemia, antidiabetic or anti-obesity properties may also be combined. More particularly, compounds belonging to one of the following classes may be combined:

PTP 1B (protein tyrosine phosphase—1B) inhibitors, VPAC 2 receptor agonists, GLK modulators, retinoid modulators, glycogen phosphorylase (HGLPa) inhibitors, glucagon antagonists, glucose-6-phosphate inhibitors, pyruvate dehydrogenase kinase (PKD) activators, RXR, FXR or LXR modulators, SGLT (sodium dependent glucose transporter) inhibitors, CETP (cholesteryl ester transfer protein) inhibitors, squalene synthetase inhibitors, squalene epoxidase inhibitors, triglyceride synthesis inhibitors, LDL (low density lipoprotein) receptor inducers, IBAT inhibitors, FBPase (fructose-1,6-biphosphatase) inhibitors, CART (cocaine-amphetamine-regulated transcript) modulators, MC4 (melanocortin 4) modulators, and orexin receptor antagonists.

In the pharmaceutical compositions of the present invention for oral, sublingual, subcutaneous, intramuscular, intravenous, topical, local, intratracheal, intranasal, transdermal or rectal administration, the active ingredient of formula (I) above, or the possible solvate or hydrate thereof, may be administered in a unit administration form, as a mixture with standard pharmaceutical excipients, to animals and to human beings for the prophylaxis or treatment of the above disorders or diseases.

The appropriate unit administration forms include forms for oral administration, such as tablets, soft or hard gel capsules, powders, granules and oral solutions or suspensions, sublingual, buccal intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, ointments or lotions.

By way of example, a unit administration form for a compound according to the invention in tablet form may comprise the following constituents.

| Compound according to the invention | 50.0 mg |
|---|---|
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

For oral administration, the dose of active ingredient administered per day may reach from 0.01 to 100 mg/kg, in one or more dosage intakes, preferably 0.02 to 50 mg/kg.

There may be specific cases where higher or lower dosages are appropriate; such dosages do not depart from the context of the invention. According to the usual practice, the dosage appropriate to each patient is determined by the physician according to the method of administration and the weight and response of said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound having the formula (I):

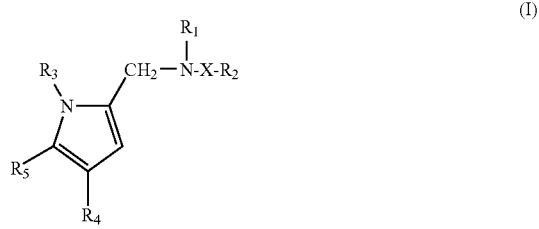

in which
x represents a group

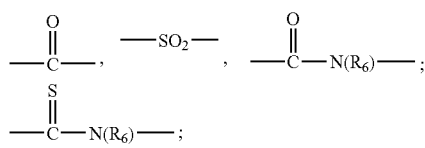

$R_1$ represents a hydrogen atom or a $(C_1-C_4)$alkyl group;
$R_2$ represents:
a $(C_1-C_{12})$alkyl which is unsubstituted or substituted one or more times with substituents chosen independently from a halogen atom, a hydroxyl, a $(C_1-C_4)$ alkoxy, a $(C_1-C_4)$alkylthio, a phenoxy, a trifluoromethoxy radical, a difluoromethoxy radical, a difluoromethylthio radical and a trifluoromethylthio radical;

a nonaromatic carbocyclic $(C_3-C_{12})$ radical which is unsubstituted or substituted one or more times with substituents chosen independently from a $(C_1-C_4)$ alkyl, a $(C_1-C_4)$alkoxy, a $(C_1-C_4)$alkylthio, a fluorine atom, a hydroxyl, a trifluoromethyl radical, a difluoromethyl radical, a trifluoromethoxy radical, a difluoromethoxy radical, a trifluoromethylthio radical and a difluoromethylthio radical;

a methyl substituted with a nonaromatic carbocyclic $(C_3-C_{12})$ radical which is unsubstituted or substituted one or more times with substituents chosen independently from a $(C_1-C_4)$alkyl, a $(C_1-C_4)$alkoxy, a $(C_1-C_4)$alkylthio, a fluorine atom, a hydroxyl, a trifluoromethyl radical, a difluoromethyl radical, a trifluoromethoxy radical, a difluoromethoxy radical, a trifluoromethylthio radical and a difluoromethylthio radical;

a phenyl, benzyl, benzhydryl or benzhydrylmethyl radical, in which each phenyl group is unsubstituted or substituted one or more times with substituents chosen independently from a halogen atom, a hydroxyl, a $(C_1-C_4)$alkyl, a $(C_1-C_4)$alkoxy, a methylenedioxy, a cyano, a nitro, a trifluoromethyl, a difluoromethyl, a difluoromethoxy, a trifluoromethoxy, a trifluoromethylthio, a difluoromethylthio, an $S(O)_n$Alk group, an $OS(O)_n$Alk group and a $(C_1-C_4)$alkylcarbonyl group;

a phenyl radical substituted with a heterocyclic radical chosen from pyrrolyl, imidazolyl, pyridyl or pyrazolyl, said heterocyclic radical being unsubstituted or substituted one or more times with one or more substituents chosen independently from a halogen atom or a $(C_1-C_4)$alkyl group;

a phenyl radical substituted with a phenyl or a phenoxy, in which each phenyl group is unsubstituted or substituted one or more times with substituents chosen independently from a halogen atom, a hydroxyl, a $(C_1-C_4)$alkyl, a $(C_1-C_4)$alkoxy, a methylenedioxy, a cyano, a nitro, a trifluoromethyl, a difluoromethyl, a difluoromethoxy, a trifluoromethoxy, a trifluoromethylthio, a difluoromethylthio, an $S(O)_n$Alk group, an $OS(O)_n$Alk group and a $(C_1-C_4)$alkylcarbonyl group;

a 1,2,3,4-tetrahydronaphthalen-$_2$-yl which is unsubstituted or substituted one or more times with a $(C_1-C_4)$ alkyl or a trifluoromethyl;

a pyrrolyl, imidazolyl, pyridyl, pyrazolyl, furyl, thienyl, oxazolyl or thiazolyl radical, said radicals being unsubstituted or substituted with one or more substituents chosen independently from a halogen atom, a $(C_1-C_4)$alkyl group or a trifluoromethyl group;

an indol-$_2$-yl or an N-methylindol-$_2$-yl;

$R_3$ represents a $(C_1-C_5)$alkyl or a $(C_3-C_7)$cycloalkyl;

$R_4$ represents a phenyl which is unsubstituted or substituted one or more times with substituents chosen independently from a halogen atom, a $(C_1-C_4)$alkyl, a $(C_1-C_4)$alkoxy, a cyano, a difluoromethyl radical, a trifluoromethyl radical, a difluoromethoxy radical, a trifluoromethoxy radical, an $S(O)_n$Alk group or an $OS(O)_n$ Alk group;

$R_5$ represents a phenyl which is unsubstituted or substituted one or more times with substituents chosen independently from a halogen atom, a $(C_1-C_4)$alkyl, a $(C_1-C_4)$alkoxy, a cyano, a difluoromethyl radical, a trifluoromethyl radical, a difluoromethoxy radical, a trifluoromethoxy radical, an $S(O)_n$Alk group or an $OS(O)_n$Alk group;

$R_6$ represents a hydrogen atom or a $(C_1-C_4)$alkyl;

n represents 0, 1 or 2; and

Alk represents a $(C_1-C_4)$alkyl; or a salt thereof.

2. The compound of formula (I) according to claim 1, wherein:

X represents a group

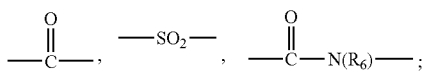

$R_1$ represents a hydrogen atom or a $(C_1-C_4)$alkyl group;

$R_2$ represents:
- a $(C_1-C_7)$alkyl;
- a nonaromatic carbocyclic $C_3-C_{12}$ radical which is unsubstituted or substituted one or more times with a $(C_1-C_4)$alkyl group;
- a methyl substituted with a nonaromatic carbocyclic $C_3-C_{12}$ radical which is unsubstituted or substituted one or more times on the carbocycle with a $(C_1-C_4)$alkyl;
- a phenyl which is unsubstituted or substituted one or more times with substituents chosen independently from a halogen atom, a $(C_1-C_4)$alkyl, a hydroxyl, a $(C_1-C_4)$alkoxy, a cyano, a trifluoromethyl group, a trifluoromethoxy group, an $S(O)_n$Alk group and a $(C_1-C_4)$alkylcarbonyl group; or from a phenyl, phenoxy, pyrrolyl, imidazolyl, pyridyl or pyrazolyl radical, said radicals being unsubstituted or substituted one or more times with a $(C_4)$alkyl;
- a benzyl which is unsubstituted or substituted one or more times on the phenyl with substituents chosen independently from a halogen atom, a cyano, a $(C_1-C_4)$alkyl, a $(C_1-C_4)$alkoxy, a trifluoromethyl radical or an $S(O)_n$Alk group; or substituted in the alpha-position with one or two similar or different groups chosen from a $(C_1-C_4)$alkyl and a $(C_3-C_7)$cycloalkyl;
- a benzhydryl or a benzhydrylmethyl group;
- a 1,2,3,4-tetrahydronaphthalen-2-yl which is unsubstituted or substituted one or more times with a $(C_1-C_4)$alkyl;
- a pyrrolyl, imidazolyl, pyridyl, pyrazolyl, furyl or thienyl radical, said radicals being unsubstituted or substituted with one or more substituents chosen independently from a halogen atom or a $(C_1-C_4)$alkyl group;
- an indol-2-yl or an N-methylindol-2-yl;

$R_3$ represents a $(C_1-C_5)$alkyl or a $(C_3-C_7)$cycloalkyl;

$R_4$ represents a phenyl which is unsubstituted or substituted one or more times with substituents chosen independently from a halogen atom, a $(C_1-C_4)$alkyl, a $(C_1-C_4)$alkoxy, a trifluoromethyl radical or an $S(O)_n$Alk group;

$R_5$ represents a phenyl which is unsubstituted or substituted one or more times with substituents chosen independently from a halogen atom, a $(C_1-C_4)$alkyl, a $(C_1-C_4)$alkoxy, a trifluoromethyl radical or an $S(O)_n$Alk group;

$R_6$ represents a hydrogen atom or a $(C_1-C_4)$alkyl;

n represents 0, 1 or 2; and

Alk represents a $(C_1-C_4)$alkyl; or a salt, thereof.

3. The compound of formula (I) according to claim 1, wherein —X— represents a —CO— group and the substituents $R_1$ to $R_5$ are as defined for the compound of formula (I) in claim 1.

4. The compound of formula (I) according to claim 1, wherein —X— represents an —$SO_2$— group and the substituents $R_1$ to $R_5$ are as defined for the compound of formula (I) in claim 1.

5. The compound of formula (I) according to claim 1, wherein —X— represents a —$CON(R_6)$— group and the substituents $R_1$ to $R_6$ are as defined for the compounds of formula (I) in claim 1.

6. A method for preparing a compound of formula (I) according to claim 1, comprising:

treating a compound of formula (II):

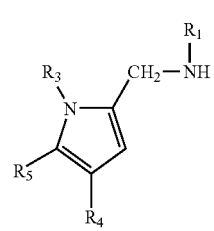

(II)

in which $R_1$, $R_3$, $R_4$ and $R_5$ are as defined for a compound of formula (I) in claim 1:

either with an acid of formula (III) or a functional derivative thereof:

HOOC—$R_2$     (III)

in which $R_2$ is as defined in claim 1, when a compound of formula (I) in which —X— represents a —CO— group is prepared;

or with a sulfonyl halide of formula (IV):

Hal-$SO_2$-$R_2$     (IV)

in which $R_2$ is as defined in claim 1 and Hal represents a halogen atom, when a compound of formula (I) in which —X— represents an —$SO_2$— group is prepared;

or with a halo formate of formula (V):

HalCOOAr     (V)

in which Hal represents a halogen atom and Ar represents a phenyl or a 4-nitrophenyl, so as to obtain an intermediate compound of formula (VI):

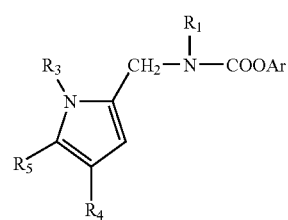

(VI)

in which $R_1$, $R_3$, $R_4$ and $R_5$ are as defined in claim 1, which is subsequently reacted with an amine of formula (VII):

$HN(R_6)R_2$     (VII)

in which $R_2$ and $R_6$ are as defined in claim 1, when a compound of formula (I) in which —X— represents a —CON($R_6$)— group is prepared;

or with an isothiocyanate of formula, $R_2$—N=C=S (IX) in which $R_2$ is as defined in claim 1, when a compound of formula (I) in which —X— represents a —CSN($R_6$)— group is prepared.

7. A compound of formula (II):

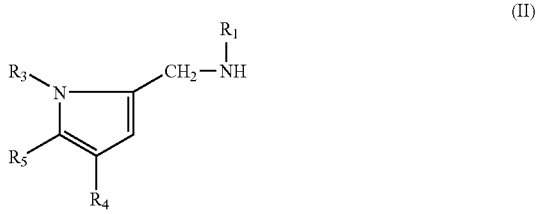

in which:

$R_1$ represents a hydrogen atom or a ($C_1$-$C_4$)alkyl group;

$R_3$ represents a ($C_1$-$C_5$)alkyl or a ($C_3$-$C_7$)cycloalkyl;

$R_4$ represents a phenyl which is unsubstituted or substituted one or more times with substituents chosen independently from a halogen atom, a ($C_1$-$C_4$)alkyl, a ($C_1$-$C_4$)alkoxy, a cyano, a difluoromethyl radical, a trifluoromethyl radical, a difluoromethoxy radical, a trifluoromethoxy radical, an S(O)$_n$Alk group or an OS(O)$_n$Alk group;

$R_5$ represents a phenyl which is unsubstituted or substituted one or more times with substituents chosen independently from a halogen atom, a ($C_1$-$C_4$)alkyl, a (Ci$_1$C$_4$)alkoxy, a cyano, a difluoromethyl radical, a trifluoromethyl radical, a difluoromethoxy radical, a trifluoromethoxy radical, an S(O)$_n$Alk group or an OS(O)$_n$Alk group;

n represents 0, 1 or 2; and

Alk represents a ($C_1$-$C_4$)alkyl.

8. A pharmaceutical composition comprising a compound of formula (I) as claimed in claim 1 or a pharmaceutically acceptable salt thereof in combination with at least one pharmaceutically acceptable excipient.

9. A pharmaceutical composition comprising a compound of formula (I) as claimed in claim 2 or a pharmaceutically acceptable salt thereof in combination with at least one pharmaceutically acceptable excipient.

10. A pharmaceutical composition comprising a compound of formula (I) as claimed in claim 3 or a pharmaceutically acceptable salt thereof in combination with at least one pharmaceutically acceptable excipient.

11. A pharmaceutical composition comprising a compound of formula (I) as claimed in claim 4 or a pharmaceutically acceptable salt thereof in combination with at least one pharmaceutically acceptable excipient.

12. A pharmaceutical composition comprising a compound of formula (I) as claimed in claim 5 or a pharmaceutically acceptable salt thereof in combination with at least one pharmaceutically acceptable excipient.

* * * * *